United States Patent
Yu et al.

(10) Patent No.: US 12,393,838 B2
(45) Date of Patent: Aug. 19, 2025

(54) VESSEL IMAGE CLASSIFICATION METHOD AND APPARATUS, DEVICE, AND STORAGE MEDIUM

(71) Applicant: TENCENT TECHNOLOGY (SHENZHEN) COMPANY LIMITED, Shenzhen (CN)

(72) Inventors: Shuang Yu, Shenzhen (CN); Wenting Chen, Shenzhen (CN); Kai Ma, Shenzhen (CN); Yefeng Zheng, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 470 days.

(21) Appl. No.: 17/994,678

(22) Filed: Nov. 28, 2022

(65) Prior Publication Data

US 2023/0106222 A1    Apr. 6, 2023

Related U.S. Application Data

(63) Continuation of application No. PCT/CN2022/087404, filed on Apr. 18, 2022.

(30) Foreign Application Priority Data

May 19, 2021    (CN) .......................... 202110547148.7

(51) Int. Cl.
*G06K 9/62*   (2022.01)
*G06N 3/08*   (2023.01)
*G06V 10/70*  (2022.01)

(52) U.S. Cl.
CPC .............. *G06N 3/08* (2013.01); *G06V 10/70* (2022.01); *G06T 2207/20081* (2013.01)

(58) Field of Classification Search
CPC ........ G06N 3/08; G06N 3/006; G06N 3/0442; G06N 3/0455; G06N 3/0464; G06T 7/20;
(Continued)

(56) References Cited

FOREIGN PATENT DOCUMENTS

| CN | 110197493 A | * | 9/2019 | .......... G06N 3/0454 |
| CN | 110211140 A |   | 9/2019 | |

(Continued)

OTHER PUBLICATIONS

International Search Report with English translation and Written Opinion regarding PCT/CN2022/087404 dated Jul. 6, 2022.

(Continued)

*Primary Examiner* — Xin Jia
(74) *Attorney, Agent, or Firm* — Crowell & Moring LLP

(57) ABSTRACT

This present disclosure relates to the technical field of artificial intelligence, and provides a vessel image classification method and apparatus, a device, and a storage medium. The method includes: inputting a first vessel image sample into a first image processing model, and obtaining a predicted enhanced image and predicted vessel location information; and training the first image processing model based on a second vessel image sample, vessel location labeling information, the predicted enhanced image, and the predicted vessel location information. In the above solution, the impact of image quality on the vessel classification is considered during training of the vessel classification model, so that an end-to-end vessel classification model subsequently generated based on the trained first image processing model can realize a higher classification accuracy for a low quality vessel image, thereby improving the accuracy of classifying vessels in the vessel image by artificial intelligence.

20 Claims, 10 Drawing Sheets

(58) Field of Classification Search
CPC . G06T 2207/20081; G06T 2207/20084; G06T 2207/30241; G06T 2207/30236; G06T 2207/30252
See application file for complete search history.

(56) References Cited

FOREIGN PATENT DOCUMENTS

| | | | | |
|---|---|---|---|---|
| CN | 110276763 A | * | 9/2019 | ............... G06T 7/11 |
| CN | 111242865 A | | 6/2020 | |
| CN | 111369542 A | * | 7/2020 | ........... G06K 9/6268 |
| CN | 111461134 A | | 7/2020 | |
| CN | 111932535 A | * | 11/2020 | ......... G06F 18/2415 |
| CN | 112966792 A | | 6/2021 | |

OTHER PUBLICATIONS

Extended European Search Report regarding EP 22 80 3717 dated Jun. 28, 2024, 9 pages.

Girard et al., "Joint segmentation and classification of retinal arteries/veins from fundus images," arxiv.org, Cornell University Library, 201 Olin Library Cornell University Ithaca, NY 14853, XP081125776, Mar. 4, 2019, 15 pages.

Ye et al., "A Decomposition-based Network for Non-uniform Illuminated Retinal Image Enhancement," 2021 15th International Symposium on Medical Information and Communication Technology (ISMICT), IEEE, XP033916171, Apr. 14, 2021, 6 pages.

* cited by examiner

201
Acquire a first vessel image sample, a second vessel image sample, and vessel position labeling information, the first vessel image sample being a low quality image corresponding to the second vessel image sample, and the vessel location labeling information indicating locations of at least two types of vessels labeled from the first vessel image sample 202
Input the first vessel image sample into a first image processing model, and obtain a predicted enhanced image and predicted vessel location information outputted by the first image processing model, the predicted enhanced image being a quality-enhanced image of the first vessel image sample; and the predicted vessel location information indicating locations of the at least two types of vessels predicted from the first vessel image sample 203
Acquire a loss function value based on the second vessel image sample, the vessel location labeling information, the predicted enhanced image, and the predicted vessel location information 204
Train the first image processing model based on the loss function value, the trained first image processing model being configured to generate a second image processing model, the second image processing model being configured to process an inputted target vessel image to output vessel classification information of the target vessel image, the vessel classification information being used for indicating a target type vessel in the target vessel image, and the target type vessel being at least one of the at least two types of vessels

FIG. 2

VESSEL IMAGE CLASSIFICATION METHOD AND APPARATUS, DEVICE, AND STORAGE MEDIUM

RELATED APPLICATION

This application is a continuation application of PCT Patent Application No. PCT/CN2022/087404, filed on Apr. 18, 2022, which claims priority to Chinese Patent Application No. 202110547148.7, filed on May 19, 2021, both of which are incorporated herein by reference in their entireties.

FIELD OF THE TECHNOLOGY

This present disclosure relates to the technical field of artificial intelligence, and in particular, to a vessel image classification method and apparatus, a device, and a storage medium.

BACKGROUND OF THE DISCLOSURE

In the medical field, quantitative analysis of retinal vessels helps find various potential cardiovascular diseases. Retinal artery or vein (A/V) classification lays a foundation for the quantitative analysis of the retinal vessels.

In the related art, the retinal A/V classification is usually realized by a pre-trained end-to-end deep learning model by processing an inputted fundus image and directly outputting locations of arteries and/or veins in the fundus image. The deep learning model is usually trained by using the fundus image sample as an input and the locations of the arteries and/or veins in the fundus image sample as labeling information.

However, quality of the captured fundus image usually cannot be guaranteed. Since a low quality fundus image affects a processing effect of the deep learning model, an accuracy of classifying the vessels in the fundus image may be relatively low.

SUMMARY

Embodiments of this present disclosure provide a vessel image classification method and apparatus, a device, and a storage medium, which can improve the accuracy of classifying vessels in an image by a model. The technical solutions are as follows.

The present disclosure describes a method for classifying a vessel image. The method includes acquiring, by a device, a first vessel image sample, a second vessel image sample, and vessel location labeling information, the first vessel image sample being a low quality image corresponding to the second vessel image sample, and the vessel location labeling information indicating locations of at least two types of vessels labeled from the first vessel image sample. The device includes a memory storing instructions and a processor in communication with the memory. The method further includes: inputting, by the device, the first vessel image sample into a first image processing model, and obtaining a predicted enhanced image and predicted vessel location information outputted by the first image processing model, the predicted enhanced image being a quality-enhanced image of the first vessel image sample, and the predicted vessel location information indicating locations of the at least two types of vessels predicted from the first vessel image sample; acquiring, by the device, a loss function value based on the second vessel image sample, the vessel location labeling information, the predicted enhanced image, and the predicted vessel location information; and training, by the device, the first image processing model based on the loss function value, the trained first image processing model being configured to generate a second image processing model, the second image processing model being configured to process a target vessel image to output vessel classification information of the target vessel image, the vessel classification information indicating a target type vessel in the target vessel image, and the target type vessel being at least one of the at least two types of vessels.

The present disclosure describes an apparatus for classifying a vessel image. The apparatus includes a memory storing instructions; and a processor in communication with the memory. When the processor executes the instructions, the processor is configured to cause the apparatus to perform: acquiring a first vessel image sample, a second vessel image sample, and vessel location labeling information, the first vessel image sample being a low quality image corresponding to the second vessel image sample, and the vessel location labeling information indicating locations of at least two types of vessels labeled from the first vessel image sample, inputting the first vessel image sample into a first image processing model, and obtaining a predicted enhanced image and predicted vessel location information outputted by the first image processing model, the predicted enhanced image being a quality-enhanced image of the first vessel image sample, and the predicted vessel location information indicating locations of the at least two types of vessels predicted from the first vessel image sample, acquiring a loss function value based on the second vessel image sample, the vessel location labeling information, the predicted enhanced image, and the predicted vessel location information, and training the first image processing model based on the loss function value, the trained first image processing model being configured to generate a second image processing model, the second image processing model being configured to process a target vessel image to output vessel classification information of the target vessel image, the vessel classification information indicating a target type vessel in the target vessel image, and the target type vessel being at least one of the at least two types of vessels.

The present disclosure describes a non-transitory computer-readable storage medium, storing computer-readable instructions. The computer-readable instructions, when executed by a processor, are configured to cause the processor to perform: acquiring a first vessel image sample, a second vessel image sample, and vessel location labeling information, the first vessel image sample being a low quality image corresponding to the second vessel image sample, and the vessel location labeling information being used for indicating locations of at least two types of vessels labeled from the first vessel image sample, inputting the first vessel image sample into a first image processing model, and obtaining a predicted enhanced image and predicted vessel location information outputted by the first image processing model, the predicted enhanced image being a quality-enhanced image of the first vessel image sample, and the predicted vessel location information being used for indicating locations of the at least two types of vessels predicted from the first vessel image sample, acquiring a loss function value based on the second vessel image sample, the vessel location labeling information, the predicted enhanced image, and the predicted vessel location information, and training the first image processing model based on the loss function value, the trained first image processing model being configured to generate a second image processing model, the second image processing model being configured to process a target vessel image to output vessel classification information of the target vessel image, the vessel classification information being used for indicating a target type vessel in the target vessel image, and the target type vessel being at least one of the at least two types of vessels.

In another aspect, a vessel image classification method is provided, including:

acquiring a first vessel image sample, a second vessel image sample, and vessel location labeling information, the first vessel image sample being a low quality image corresponding to the second vessel image sample, and the vessel location labeling information being used for indicating locations of at least two types of vessels labeled from the first vessel image sample;

inputting the first vessel image sample into a first image processing model, and obtaining a predicted enhanced image and predicted vessel location information outputted by the first image processing model, the predicted enhanced image being a quality-enhanced image of the first vessel image sample; and the predicted vessel location information being used for indicating locations of the at least two types of vessels predicted from the first vessel image sample;

acquiring a loss function value based on the second vessel image sample, the vessel location labeling information, the predicted enhanced image, and the predicted vessel location information; and training the first image processing model based on the loss function value, the trained first image processing model being configured to generate a second image processing model, the second image processing model being configured to process an inputted target vessel image to output vessel classification information of the target vessel image, the vessel classification information being used for indicating a target type vessel in the target vessel image, and the target type vessel being at least one of the at least two types of vessels.

In another aspect, a vessel image classification method is provided, including:

acquiring a target vessel image;

inputting the target vessel image into a second image processing model, and obtaining vessel location information outputted by the second image processing model, the vessel location information indicating at least a location of a target type vessel predicted from the target vessel image; and outputting a vessel classification result image based on the vessel location information, the vessel classification result image being used for indicating the target type vessel in the target vessel image; and the second image processing model being generated based on a trained first image processing model; a loss function value for training the first image processing model being acquired based on a second vessel image sample, vessel location labeling information, a predicted enhanced image, and predicted vessel location information; the predicted enhanced image and the predicted vessel location information being outputted by the first image processing model after processing the first vessel image sample; the first vessel image sample being a low quality image corresponding to the second vessel image sample, and the vessel location labeling information being used for indicating locations of at least two types of vessels labeled from the first vessel image sample; the predicted enhanced image being a quality-enhanced image of the first vessel image sample; and the predicted vessel location information being used for indicating locations of the at least two types of vessels predicted from the first vessel image sample.

In still another aspect, a vessel image classification apparatus is provided, including:

a sample acquisition module, configured to acquire a first vessel image sample, a second vessel image sample, and vessel location labeling information, the first vessel image sample being a low quality image corresponding to the second vessel image sample, and the vessel location labeling information being used for indicating locations of at least two types of vessels labeled from the first vessel image sample;

a prediction module, configured to input the first vessel image sample into a first image processing model, and obtain a predicted enhanced image and predicted vessel location information outputted by the first image processing model, the predicted enhanced image being a quality-enhanced image of the first vessel image sample; and the predicted vessel location information being used for indicating locations of the at least two types of vessels predicted from the first vessel image sample;

a loss acquisition module, configured to acquire a loss function value based on the second vessel image sample, the vessel location labeling information, the predicted enhanced image, and the predicted vessel location information; and a training module, configured to train the first image processing model based on the loss function value, the trained first image processing model being configured to generate a second image processing model, the second image processing model being configured to process an inputted target vessel image to output vessel classification information of the target vessel image, the vessel classification information being used for indicating a target type vessel in the target vessel image, and the target type vessel being at least one of the at least two types of vessels.

In yet another aspect, a vessel image classification apparatus is provided, including:

an image acquisition module, configured to acquire a target vessel image;

a model processing module, configured to input the target vessel image into a second image processing model, and obtain vessel location information outputted by the second image processing model, the vessel location information indicating at least a location of a target type vessel predicted from the target vessel image; and an output module, configured to output a vessel classification result image based on the vessel location information, the vessel classification result image being used for indicating the target type vessel in the target vessel image; and the second image processing model being generated based on a trained first image processing model; a loss function value for training the first image processing model being acquired based on a second vessel image sample, vessel location labeling information, a predicted enhanced image, and predicted vessel location information; the predicted enhanced image and the predicted vessel location information being outputted by the first image processing model after processing the first vessel image sample; the first vessel image sample being a low quality image corresponding to the second vessel image sample, and the vessel location labeling information being used for indicating locations of at least two types of vessels labeled from the first vessel image sample; the predicted enhanced image being a quality-enhanced image of the first vessel image sample; and the predicted vessel location information being used for indicating locations of the at least two types of vessels predicted from the first vessel image sample.

According to another aspect, a computer device is provided, and includes a processor and a memory, the memory storing at least one computer instruction, the at least one computer instruction being loaded and executed by the processor to implement the vessel image classification method.

According to another aspect, a computer-readable storage medium is provided, storing at least one computer instruction, the at least one computer instruction being loaded and executed by a processor to implement the vessel image classification method.

According to another aspect, a computer program product is provided, the computer program product including computer instructions, the computer instructions being stored in a computer-readable storage medium. A processor of a computer device reads the computer instructions from the computer-readable storage medium, and executes the computer instructions, to cause the computer device to perform the foregoing vessel image classification method.

During the training, the first image processing model performs vessel location prediction and image quality enhancement on the inputted first vessel image sample, and the first image processing model is trained by using the high quality second vessel image sample, the vessel location labeling information, the predicted enhanced image, and the predicted vessel location information. That is to say, the impact of image quality on the vessel classification is considered during the training of the vessel classification model, so that an end-to-end vessel classification model subsequently generated based on the trained first image processing model can realize a higher classification accuracy for a low quality vessel image, thereby improving the accuracy of classifying vessels in the vessel image.

BRIEF DESCRIPTION OF THE DRAWINGS

FIG. 2 is a schematic flowchart of a vessel image classification method according to an exemplary embodiment.

DESCRIPTION OF EMBODIMENTS

Figure 1:
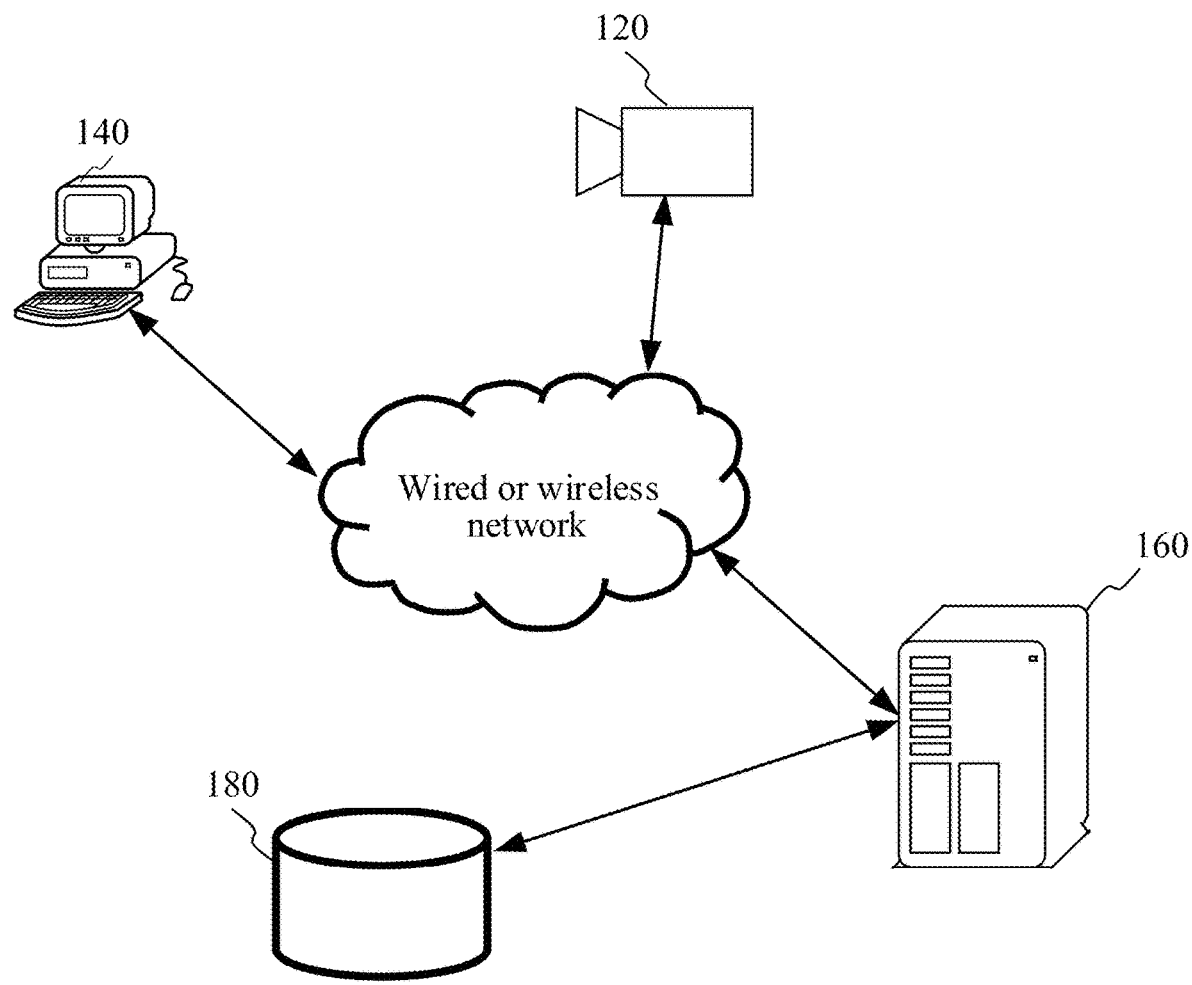
FIG. 1 is a system composition diagram of a vessel classification system in various embodiments of this present disclosure.

FIG. 1 is a system composition diagram of a vessel classification system in various embodiments of this present disclosure. The system includes a medical image capture device 120, a terminal 140, and a server 160. In some implementations, the system may further include a database 180.

The medical image capture device 120 may be a camera device or a video camera device configured to capture a vessel image. The vessel image is a medical image that includes vessels. For example, the vessel image may be a fundus image (including vessels under a retina), a gastroscopic image, a colonoscopic image, an intra-oral image, or the like.

The medical image capture device 120 may include an image output interface, such as a universal serial bus (USB) interface, a high definition multimedia interface (HDMI), or an Ethernet interface. Alternatively, the image output interface may be a wireless interface, such as a wireless local area network (WLAN) interface or a Bluetooth interface.

An operator may export a microscopic image captured by the camera in various manners in response to different types of image output interfaces. For example, the microscopic image is imported to the terminal 140 in a wired or short-range wireless manner. Alternatively, the microscopic image may be imported to the terminal 140 or the server 160 through a local area network or the Internet.

The terminal 140 may be a terminal device having a certain processing capacity and an interface display function. For example, the terminal 140 may be a mobile phone, a tablet computer, an e-book reader, smart glasses, a laptop portable computer, a desktop computer, or the like.

The terminal 140 may include a terminal for use by developers and medical personnel.

When the terminal 140 is implemented as the terminal for use by the developers, the developers may develop, through the terminal 140, a machine learning model for recognizing vessels in the vessel image and deploy the machine learning model to the server 160 or to the terminal used by the medical personnel.

When the terminal 140 is implemented as the terminal for use by the medical personnel, an application configured to acquire and present a vessel classification result of the vessel image may be installed in the terminal 140. After acquiring the vessel image captured by the medical image capture device 120, the terminal 140 may acquire a processing result of the vessel image through the application and present the processing result, so that a doctor can perform pathological diagnosis and other operations.

In the system shown in FIG. 1, the terminal 140 and the medical image capture device 120 are physically separated physical devices. In some implementations, when the terminal 140 is implemented as the terminal for use by the medical personnel, the terminal 140 and the medical image capture device 120 may be integrated as a single physical device. For example, the terminal 140 may be a terminal device having an image capture function.

The server 160 may be an independent physical server, or may be a server cluster or a distributed system formed by a plurality of physical servers, or may be a cloud server that provides basic cloud computing services such as a cloud service, a cloud database, cloud computing, a cloud function, cloud storage, a network service, cloud communication, a middleware service, a domain name service, a security service, a content delivery network (CDN), big data, and an AI platform.

The server 160 may be a server that provides a background service for the application installed in the terminal 140. The background server may perform version management of the application, perform background processing of the vessel image acquired by the application and return a processing result, perform background training of the machine learning model developed by the developers, and the like.

The database 180 may be a Redis database, or may be any other type of database. The database 180 is configured to store various types of data.

In some implementations, the terminal 140 is connected to the server 160 by a communication network. In some implementations, the medical image acquisition device 120 is connected to the server 160 by a communication network. In some implementations, the communications network is a wired network or a wireless network.

In some implementations, the system may further include a management device (not shown in FIG. 1). The management device is connected to the server 160 through a communication network. In some implementations, the communication network is a wired network or a wireless network.

In some implementations, the wireless network or the wired network uses a standard communication technology and/or protocol. The network is usually the Internet, but may alternatively be any other networks, including but not limited to a local area network (LAN), a metropolitan area network (MAN), a wide area network (WAN), a mobile, wired, or wireless network, or any combination of a dedicated network or a virtual dedicated network. In some embodiments, technologies and/or formats such as hypertext markup language (HTML) and extensible markup language (XML) are used to represent data exchanged through a network. In addition, all or some links may be encrypted by using common encryption technologies such as a secure sockets layer (SSL), a transport layer security (TLS), a virtual private network (VPN), and an Internet protocol security (IPsec). In some other embodiments, custom and/or dedicated data communication technologies may also be used in place of or in addition to the foregoing data communication technologies.

FIG. 2 is a schematic flowchart of a vessel image classification method according to an exemplary embodiment. The method may be performed by a computer device. For example, the computer device may be a server, or may be a terminal, or may include a server and a terminal. The server may be the server 160 in the above embodiment shown in FIG. 1, and the terminal may be the terminal 140 for use by the developers in the above embodiment shown in FIG. 1. The computer device may be implemented as a model training device for model training. As shown in FIG. 2, the vessel image classification method may include the following steps.

Step 201: Acquire a first vessel image sample, a second vessel image sample, and vessel location labeling information, the first vessel image sample being a low quality image corresponding to the second vessel image sample, and the vessel location labeling information indicating locations of at least two types of vessels labeled from the first vessel image sample.

The expression the first vessel image sample being a low quality image corresponding to the second vessel image sample may mean that the first vessel image sample and the second vessel image sample have same image content and image quality of the first vessel image sample is lower than that of the second vessel image sample.

In some implementations, the first vessel image sample may be different from the second vessel image sample in resolution, detail rendition, color rendition, contrast, and the like.

In some implementations, the first vessel image sample is obtained by degrading the second vessel image sample.

The vessel location labeling information may be information pre-labeled by the developers based on the second vessel image sample. In some implementations, the vessel location labeling information may be information for indicating locations of at least two types of vessels labeled from the second vessel image sample.

In a possible implementation, the vessel location labeling information may be a masked image having at least two channels. Each channel of the masked image is used for indicating a location of a type of vessel in the corresponding vessel image. In some implementations, the vessel location labeling information may include at least two mask channels, and each of the at least two mask channels corresponds to each of the at least two types of vessels, respectively.

In another possible implementation, the vessel location labeling information may be coordinate information. For example, the coordinate information may include at least two coordinate sets. Each of the coordinate sets includes location coordinates (such as pixel coordinates) of a type of vessel in a corresponding vessel image.

In this embodiment of this present disclosure, the at least two types of vessels may include at least two of an arterial vessel, a venous vessel, and an integral vessel (that is, all vessels including the arterial vessel and the venous vessel).

Step 202: Input the first vessel image sample into a first image processing model, and obtain a predicted enhanced image and predicted vessel location information outputted by the first image processing model, the predicted enhanced image being a quality-enhanced image of the first vessel image sample; and the predicted vessel location information indicating locations of the at least two types of vessels predicted from the first vessel image sample.

In this embodiment of this present disclosure, the first image processing model is a to-be-trained machine learning model pre-built by the developers. For example, the first image processing model may be a deep learning model.

The first image processing model includes at least one input port and two output ports. During the training, the input port is configured to be inputted with the first vessel image sample. Then the first image processing model is configured to perform the following processes on the first vessel image sample. A first process is to predict the locations of the at least two types of vessels in the first vessel image sample (that is to say, during the prediction of the vessel locations in the first vessel image sample, the vessels corresponding to the predicted vessel locations are further classified) and output the predicted vessel location information through one of the output ports. The other process is to enhance the image quality of the first vessel image sample and output the predicted enhanced image through the other of the output ports.

The predicted vessel location information and the vessel location labeling information may be the same type of information. For example, the predicted vessel location information and the vessel location labeling information are both a masked image or coordinate information. Alternatively, the predicted vessel location information and the vessel location labeling information may be different types of information. For example, the predicted vessel location information is a masked image, and the vessel location labeling information is coordinate information. In another example, the predicted vessel location information is coordinate information, and the vessel location labeling information is a masked image.

Step 203: Acquire a loss function value based on the second vessel image sample, the vessel location labeling information, the predicted enhanced image, and the predicted vessel location information In this embodiment of this present disclosure, the computer device may perform a loss function calculation by using the second vessel image sample, the vessel location labeling information, the predicted enhanced image, and the predicted vessel location information, to obtain the loss function value for training the first image processing model.

Step 204: Train the first image processing model based on the loss function value, the trained first image processing model being configured to generate a second image processing model, the second image processing model being configured to process an inputted target vessel image to output vessel classification information of the target vessel image, the vessel classification information being used for indicating a target type vessel in the target vessel image, and the target type vessel being at least one of the at least two types of vessels.

In conclusion, in the solution shown in this embodiment of this present disclosure, during the training, the first image processing model performs vessel location prediction and image quality enhancement on the inputted first vessel image sample, and the first image processing model is trained by using the high quality second vessel image sample, the vessel location labeling information, the predicted enhanced image, and the predicted vessel location information. That is to say, the impact of image quality on the vessel classification is considered during the training of the vessel classification model, so that an end-to-end vessel classification model subsequently generated based on the trained first image processing model can realize a higher classification accuracy for a low quality vessel image, thereby improving the accuracy of classifying vessels in the vessel image.

After the first image processing model is trained based on the above embodiment shown in FIG. 2, the second image processing model generated based on the first image processing model may be applied to a plurality of scenarios of processing images including vessels and classifying the vessels therein. For example, the second image processing model may be applied to end-to-end classification of vessels in a fundus image, a gastroscopic image, a colonoscopic image, or an intra-oral image. For a process of the application of the second image processing model to the vessel classification, refer to the following embodiments.

Figure 3:
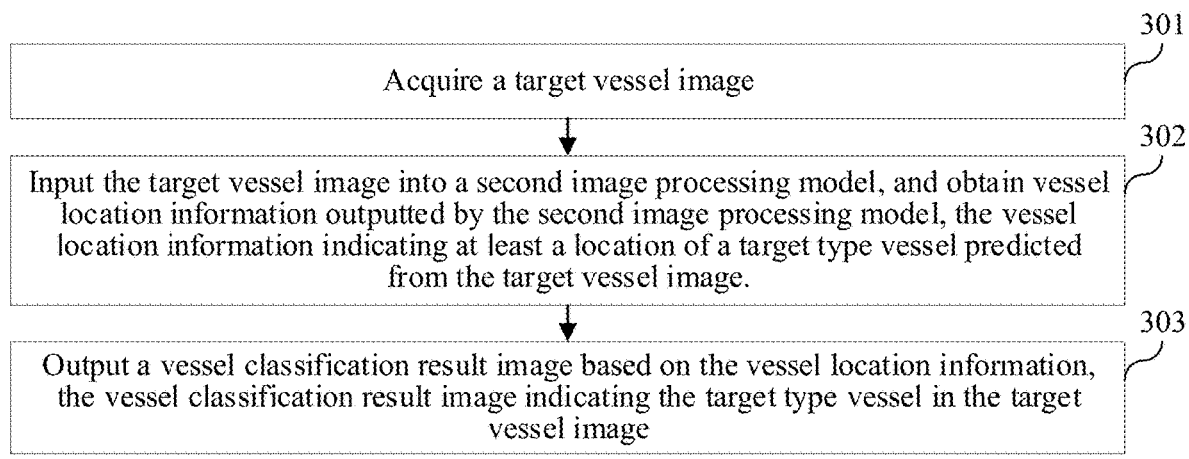
FIG. 3 is a schematic flowchart of a vessel image classification method according to an exemplary embodiment.

FIG. 3 is a schematic flowchart of a vessel image classification method according to an exemplary embodiment. The method may be performed by a computer device. For example, the computer device may be a server, or may be a terminal, or may include a server and a terminal. The server may be the server 160 in the above embodiment shown in FIG. 1, and the terminal may be the terminal 140 for use by the medical personnel in the above embodiment shown in FIG. 1. The computer device may be implemented as a model application device for performing vessel classification. As shown in FIG. 3, the vessel image classification method may include the following steps.

Step 301: Acquire a target vessel image.

The target vessel image is used for vessel localization and vessel type recognition. For example, the target vessel image is a fundus image captured by using a terminal, or may be a gastroscopic image captured by using a medical instrument.

Step 302: Input the target vessel image into a second image processing model, and obtain vessel location information outputted by the second image processing model, the vessel location information indicating at least a location of a target type vessel predicted from the target vessel image.

The vessel location information may be a masked image or coordinate information.

Step 303: Output a vessel classification result image based on the vessel location information, the vessel classification result image indicating the target type vessel in the target vessel image.

In a possible implementation, the vessel classification result image may be an image with the target type vessel being labeled based on the target vessel image. For example, the vessel classification result image may be an image with arterial/venous vessels being labeled from the target vessel image (for example, arteries and veins are labeled with different colors).

The second image processing model is generated based on the trained first image processing model; a loss function value for training the first image processing model is acquired based on a second vessel image sample, vessel location labeling information, a predicted enhanced image, and predicted vessel location information; the predicted enhanced image and the predicted vessel location information are outputted by the first image processing model after processing the first vessel image sample; the first vessel image sample is a low quality image corresponding to the second vessel image sample, and the vessel location labeling information is used for indicating locations of at least two types of vessels labeled from the first vessel image sample; the predicted enhanced image is a quality-enhanced image of the first vessel image sample; and the predicted vessel location information being used for indicating locations of the at least two types of vessels predicted from the first vessel image sample.

In conclusion, in the solution shown in this embodiment of this present disclosure, the second image processing model is generated based on the first image processing model, and during the training of the first image processing model, the first image processing model performs vessel location prediction and image quality enhancement on the inputted first vessel image sample, and the first image processing model is trained by using the high quality second vessel image sample, the vessel location labeling information, the predicted enhanced image, and the predicted vessel location information. That is to say, the impact of image quality on the vessel classification is considered during the training of the vessel classification model, so that an end-to-end vessel classification model subsequently generated based on the trained first image processing model can realize a higher classification accuracy for a low quality vessel image, thereby improving the accuracy of classifying vessels in the vessel image.

Figure 4:
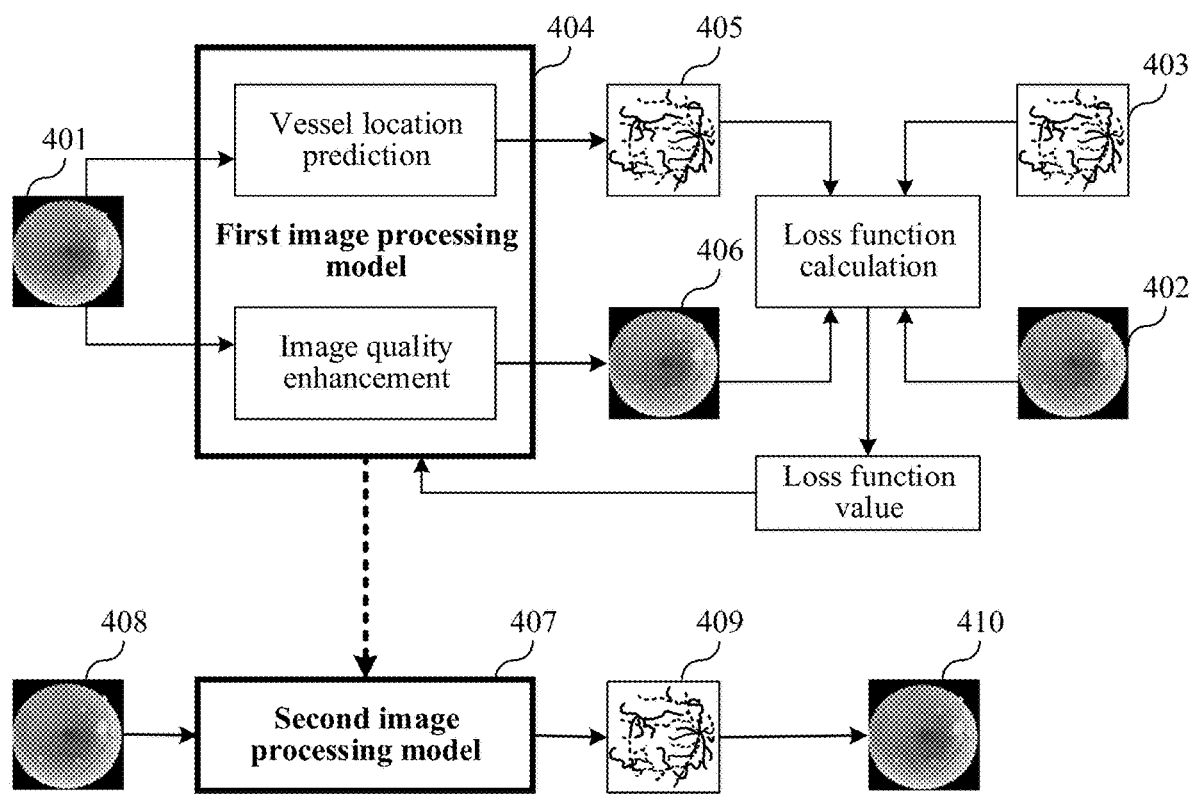
FIG. 4 is a framework diagram of processing of vessel image classification according to an exemplary embodiment.

The processing solution for vessel image classification in this present disclosure may be divided into two phases: a model training phase and a model application phase. FIG. 4 is a framework diagram of processing of vessel image classification according to an exemplary embodiment. The process of the vessel image classification is as follows.

A computer device acquires a low quality first vessel image sample 401, a high quality second vessel image sample 402, and vessel location labeling information 403 corresponding to the first vessel image sample 401. The vessel location labeling information 403 indicates locations of a plurality of types of vessels in a to-be-recognized object indicated by the first vessel image sample 401.

In the model training phase, the computer device inputs the first vessel image sample 401 into a first image processing model 404. The first image processing model 404 is configured to perform vessel location prediction and image quality enhancement on the first vessel image sample 401, and respectively output predicted vessel location information 405 and a predicted enhanced image 406 after the quality enhancement. The predicted vessel location information 405 also indicates the locations of the plurality of types of vessels predicted from the first vessel image sample 401. Then the computer device calculates a loss function value through the second vessel image sample 402, the vessel location labeling information 403, the predicted vessel location information 405, and the predicted enhanced image 406, and trains the first image processing model 404 through the loss function value. The above training process is repeated until the training of the first image processing model 404 is completed (for example, a convergence condition is satisfied).

After the first image processing model 404 is trained, the computer device may automatically generate or operated by the developers to generate a second image processing model 407 based on the first image processing model 404, and deploy the second image processing model 407.

In the model application phase, the computer device inputs a target vessel image 408 to the second image processing model 407, and the second image processing model 407 outputs vessel location information 409. Then the computer device may output a vessel classification result image 410 for indicating the target type vessel in the target vessel image based on the vessel location information 409, so that the medical personnel can make corresponding decision/judgment based on the vessel classification result image 410.

Figure 5:
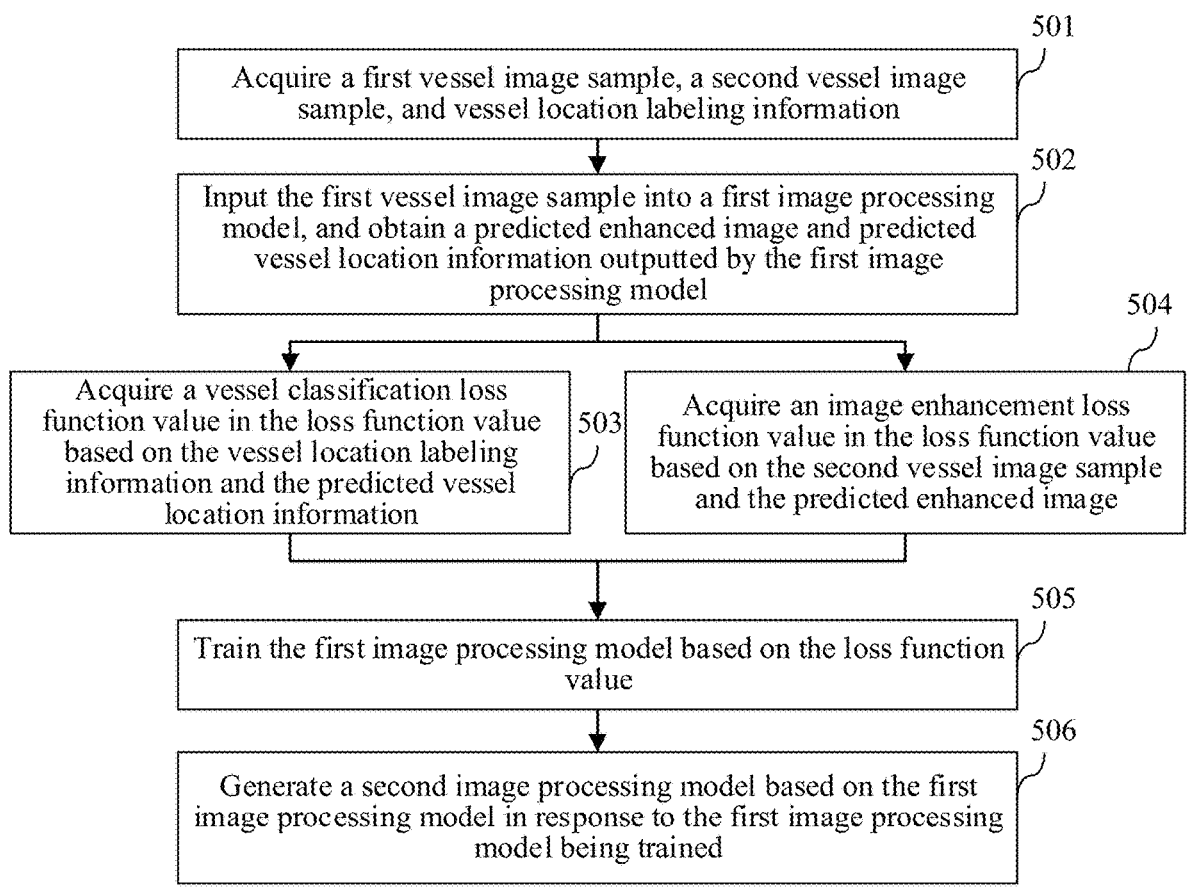
FIG. 5 is a schematic flowchart of a vessel image classification method according to an exemplary embodiment.

FIG. 5 is a schematic flowchart of a vessel image classification method according to an exemplary embodiment. As shown in FIG. 5, the vessel image classification method may include the following steps.

Step 501: Acquire a first vessel image sample, a second vessel image sample, and vessel location labeling information,
the first vessel image sample is a low quality image corresponding to the second vessel image sample, and the vessel location labeling information is used for indicating locations of at least two types of vessels labeled from the first vessel image sample.

In a possible implementation, a computer device may obtain the low quality first vessel image sample by degrading the high quality second vessel image sample.

The computer device may degrade the second vessel image sample by simulating a degradation model with a factor such as uneven illumination, image blurring, and artifacts, to obtain the first vessel image sample. Then developers label a plurality of types of vessels in the second vessel image sample, for example, and respectively labels arterial vessels and venous vessels in the second vessel image sample, to obtain the vessel location labeling information indicating the locations of the at least two types of vessels.

Step 502: Input the first vessel image sample into a first image processing model, and obtain a predicted enhanced image and predicted vessel location information outputted by the first image processing model,
the predicted enhanced image being a quality-enhanced image of the first vessel image sample; and the predicted vessel location information being used for indicating locations of the at least two types of vessels predicted from the first vessel image sample.

After the computer device inputs the first vessel image sample into the first image processing model, the first vessel image sample may be processed by an image segmentation branch in the first image processing model, and the predicted vessel location information outputted by the image segmentation branch is obtained; and the first vessel image sample is processed by an image enhancement branch in the first image processing model, and the predicted enhanced image outputted by the image enhancement branch is obtained.

In this embodiment of this present disclosure, the first image processing model may include two branches, that is, the image segmentation branch and the image enhancement branch. The image segmentation branch is configured for vessel classification, that is, to predict locations of a plurality of types of vessels in an input image. The image enhancement branch is configured to improve image quality of the input image. After the first vessel image sample is inputted into the first image processing model, the first image processing model processes the first vessel image sample in parallel through the image segmentation branch and the image enhancement branch, and respectively outputs the predicted enhanced image and the predicted vessel location information.

In a possible implementation, the image segmentation branch and the image enhancement branch share a coder, the image segmentation branch further includes a first decoder, and the image enhancement branch further includes a second decoder. That is to say, the image segmentation branch is composed of the coder and the first decoder, and the image enhancement branch is composed of the coder and the second decoder.

The expression the image segmentation branch and the image enhancement branch share a coder may mean sharing the coder as a model component. For example, the image segmentation branch and the image enhancement branch have only one coder component, and the image segmentation branch and the image enhancement branch respectively invoke the coder component for image processing.

Alternatively, the expression the image segmentation branch and the image enhancement branch share a coder may mean sharing parameters of the coder. For example, the image segmentation branch and the image enhancement branch each have a coder component, and parameters of the coders in the two coder components are the same.

Figure 6:
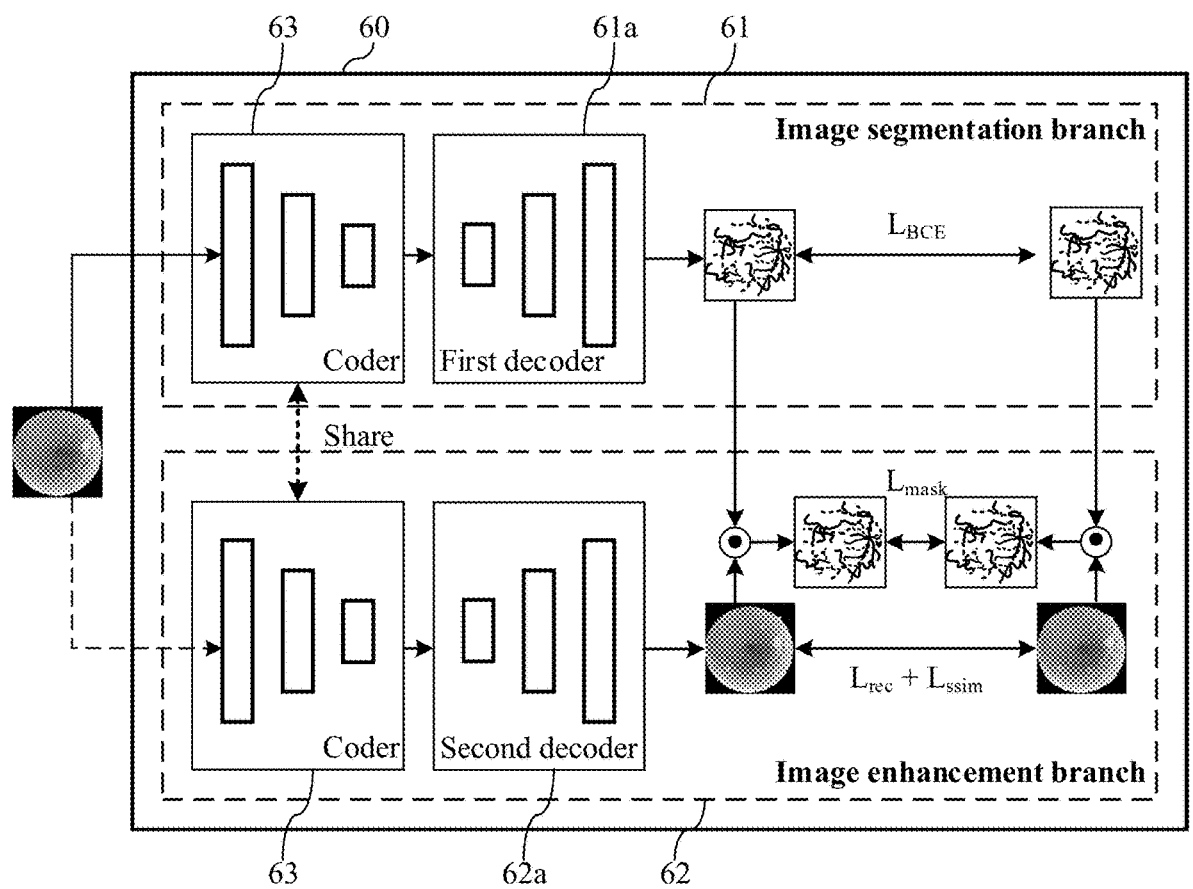
FIG. 6 is a model framework diagram of a first image processing model in the embodiment shown in FIG. 5.

FIG. 6 is a model framework diagram of a first image processing model in an embodiment of this present disclosure. As shown in FIG. 6, the first image processing model 60 is a dual-branch network with an overall architecture including two branches: an image segmentation branch 61 and an image enhancement branch 62. The image segmentation branch 61 includes a first decoder 61a, and the image enhancement branch 62 includes a second decoder 62a. In addition, the image segmentation branch 61 and the image enhancement branch 62 share a coder 63.

In FIG. 6, the image segmentation branch 61 is configured for location prediction and classification of the vessels in the input image, for example, is configured to generate an artery or vein (A/V) classification masked image, and the image enhancement branch 62 is configured to reconstruct a high quality image based on the inputted low quality image. In addition, the two branches share the same coder and have different decoders configured to simultaneously perform the A/V classification and the image enhancement. Each high quality image may be processed by a degradation model to obtain a low quality image as an input image and to obtain a real high quality image and a true value A/V classification mask to train the image enhancement branch and the image segmentation branch respectively.

The image segmentation branch may use a U-Net structure, and use a pre-trained ResNet18 as the coder. The decoder generates a three-channel probability map for segmentation of arteries, veins, and all vessels.

The image enhancement branch may alternatively be a coder-decoder-based network and share the same coder with the image segmentation branch, so as to encourage the coder to extract a feature that is relevant to the A/V classification and is robust to the image degradation. The image enhancement branch is intended to reconstruct a high quality original image from the intentionally degraded low quality image.

In this embodiment of this present disclosure, during the processing of the first vessel image sample through the first image processing model to obtain the predicted enhanced image outputted by the first image processing model and the predicted vessel location information, the computer device may divide the first vessel image sample into patches and successively input the patches to the first image processing model to obtain predicted enhanced image patches and predicted vessel location information patches respectively corresponding to the first vessel image sample patches, merges the predicted enhanced image patches respectively corresponding to the first vessel image sample patches to obtain the predicted enhanced image, and merges the predicted vessel location information patches corresponding to the first vessel image sample patches to obtain the predicted vessel location information.

Figure 7:
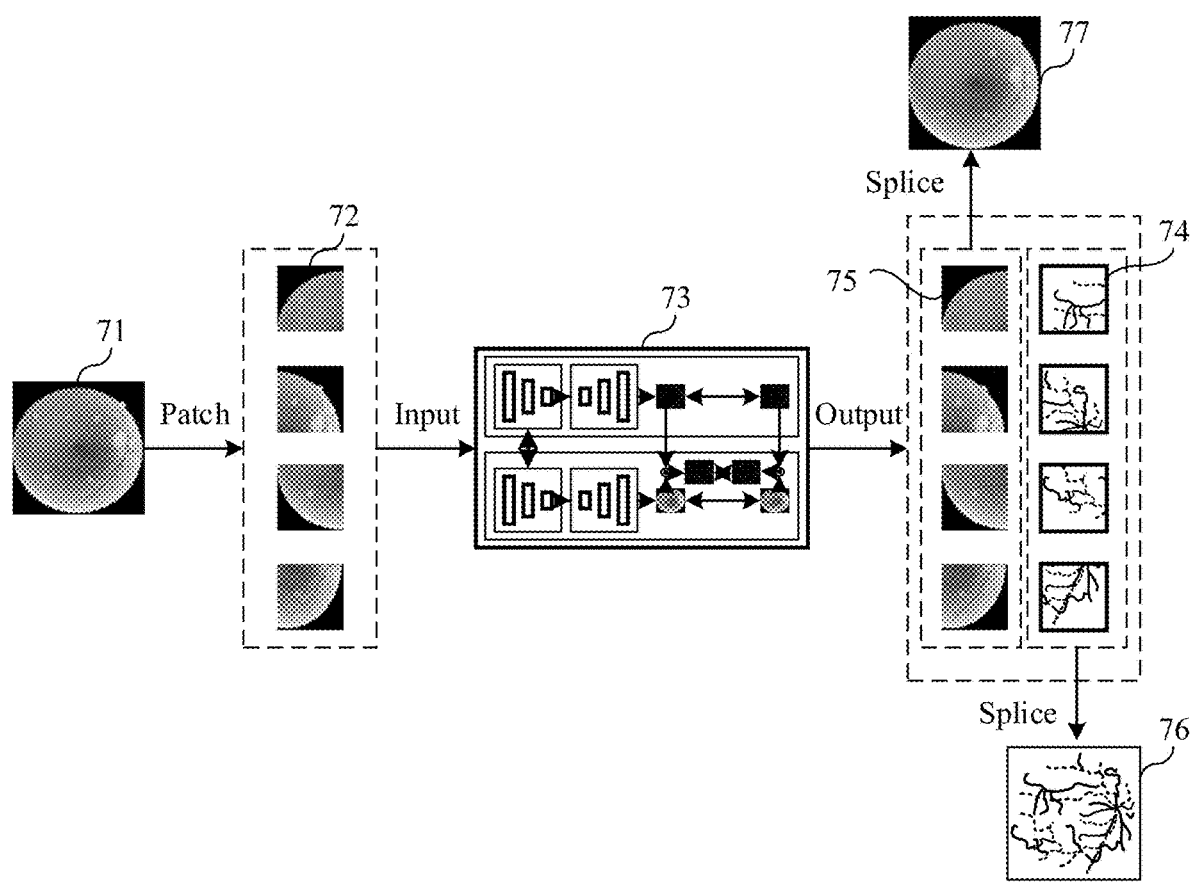
FIG. 7 is a schematic diagram of an input and an output of the model in the embodiment shown in FIG. 5.

Taking the predicted vessel location information being a masked image as an example, FIG. 7 shows a schematic diagram of an input and an output of a model in an embodiment of this present disclosure. As shown in FIG. 7, during the training, for the first vessel image sample 71, the computer device extracts one image sample patch 72 each time, and inputs the extracted image sample patch 72 into the first image processing model 73, and the first image processing model 73 outputs a predicted masked image patch 74 and a predicted enhanced image patch 75 corresponding to the image sample patch 72. Finally, the computer device splices the predicted masked image patches 74 according to an input order of the image samples 72 to obtain a predicted masked image 76, and splices the predicted enhanced image patches 75 to obtain a predicted enhanced image 77.

For example, during the training, random patch extraction is performed on the first vessel image sample (such as a low quality fundus color photograph) and corresponding artery and vein labels, and then the extracted patch is fed into the network (the first image processing model) for prediction. A result outputted by the network is a reconstructed high quality image and a predicted three-channel masked image. The predicted masked image includes an arterial vessel image, a venous vessel image, and all vessel images. Finally, the network output results corresponding to the predicted patches are spliced according to an original extraction order, that is to say, a final predicted enhanced image and an artery or vein (AV) classification result are obtained.

In this embodiment of this present disclosure, using the image patches extracted from the low quality first vessel image sample as input data to perform the model training can increase an effective training number.

The computer device may acquire a loss function value based on the second vessel image sample, the vessel location labeling information, the predicted enhanced image, and the predicted vessel location information. In some implementations, the loss function value may include a weighted combination (e.g., a weighted summation) of a vessel classification loss function value and an image enhancement loss function value. The weights for each of the vessel classification loss function value and the image enhancement loss function value may depend on importance of information. In some implementations, the weights may be learned by the image processing model. In some implementations, the weights may be pre-set.

For the process, refer to the subsequent step 503 and step 504.

Step 503: Acquire a vessel classification loss function value in the loss function value based on the vessel location labeling information and the predicted vessel location information In this embodiment of this present disclosure, the computer device may calculate a difference between the vessel location labeling information and the predicted vessel location information to obtain the vessel classification loss function value in the loss function value.

In a possible implementation, the computer device may calculate a pixel-level distance between the generated mask and the real mask by using a binary cross-entropy loss. A formula is as follows:

$$L_{BCE} = -\sum_{c=1}^{3} \mu_c L_c \log(D_1(E|(x))). \qquad (1)$$

x represents a low quality input image (that is, the first vessel image sample), $L_c$ represents a real A/V classification masked image of a class c (corresponding to the above vessel location labeling information), E and $D_1$ respectively represent the coder and the decoder of the image segmentation branch, and $D_1(E|(x))$ represents a probability map of a channel outputted by the image segmentation branch. A weight $\mu_c$ may be set to 0.4, 0.3 and 0.3 for all vessels, arteries, and veins respectively.

When the vessel location labeling information or the predicted vessel location information is not the masked image, the computer device may first convert the vessel location labeling information or the predicted vessel location information to the masked image, and then calculate a vessel classification loss function value $L_{BCE}$ through the above formula 1.

Step 504: Acquire an image enhancement loss function value in the loss function value based on the second vessel image sample and the predicted enhanced image.

In this embodiment of this present disclosure, the computer device may calculate a difference between the second vessel image sample and the predicted enhanced image to obtain the image enhancement loss function value in the loss function value.

In a possible implementation, the acquisition of the image enhancement loss function value in the loss function value based on the second vessel image sample and the predicted enhanced image includes:

acquiring a sub-loss function value based on the second vessel image sample and the predicted enhanced image, the sub-loss function value including at least one of a first sub-loss function value, a second sub-loss function value, and a third sub-loss function value; and acquiring the image enhancement loss function value based on the sub-loss function value, the first sub-loss function value being used for indicating an overall difference between the second vessel image sample and the predicted enhanced image;

the second sub-loss function value being used for indicating a visual perception difference between the second vessel image sample and the predicted enhanced image; and the third sub-loss function value being used for indicating an image difference between vessel sites respectively corresponding to the second vessel image sample and the predicted enhanced image.

More types of sub-loss function values bring higher training efficiency of the model and higher robustness of the model.

In this embodiment of this present disclosure, an L1 loss may be used as a reconstruction loss to calculate an overall similarity (corresponding to the first sub-loss function value) between the low quality image and the corresponding high quality image through the following formula:

$$L_{rec}=\|D_2(E|(x))-y\|_1 \qquad (2).$$

$D_2$ represents the decoder of the image enhancement branch, and y represents a real high quality image (such as the second vessel image sample).

In order to further maintain a structural similarity (SSIM) between the low quality image and the high quality real image, this present disclosure may further introduce a perceptual image quality loss based on visual perception (corresponding to the second sub-loss function value). The SSIM loss is calculated as follows:

$$L_{ssim}=-SSIM(D_2(E|(x)),y) \qquad (3)$$

$$SSIM(I_1, I_2) = \frac{(2\mu_1\mu_2 + C_1)(2\sigma_{12} + C_2)}{(\mu_1^2 + \mu_2^2 + C_1)(\sigma_1^2 + \sigma_2^2 + C_2)}. \qquad (4)$$

$\mu_i$ and $\sigma_i^2$ respectively represent a mean and a variance of an image $I_i$. $\sigma_{12}$ represents a covariance of $I_1$ and $I_2$. $C_1$ and $C_2$ are constants used for stability calculation (for example, $C_1=0.01\times255^2$ and $C_2=0.03\times255^2$).

In addition to the reconstruction loss and the SSIM loss, the embodiments of this present disclosure further provide a mask loss (corresponding to the above third sub-loss function value) to enhance the image reconstruction quality near vessel regions. Since a main task of this present disclosure is the vessel classification, quality of the generated image of the vessel regions is more important than a background pixel.

In a possible implementation, when the sub-loss function value includes the third sub-loss function value, the acquiring a sub-loss function value based on the second vessel image sample and the predicted enhanced image includes:

acquiring a first local image based on the second vessel image sample and the vessel location labeling information, the first local image being an image of a vessel site in the second vessel image sample;

acquiring a second local image based on the predicted enhanced image and the predicted vessel location information, the second local image being an image of a vessel site in the predicted enhanced image; and acquiring the third sub-loss function value based on the first local image and the second local image.

In order to obtain the vessel region in the enhanced image, the computer device multiplies elements of the generated vessel mask by elements of the enhanced image to obtain a first masked image $M_1$ related to the enhanced image. Similarly, a second masked image M2 related to the real image may be obtained by element-wise multiplication of the real vessel mask and the real high quality image. Then, the mask loss is constructed by optimizing the L1 loss between $M_1$ and M2 for pixel points located in the real vessel region. The calculation of the mask loss is shown as follows:

$$M_1=D_1(E(x))\odot D_2(E(x)) \qquad (5)$$

$$M_2=L\odot y \qquad (6)$$

$$L_{mask} = \frac{1}{\|L\|}\sum_{j|L_j=1}\|M_{1j} - |M_{2j}\|_1. \qquad (7)$$

L represents the true vessel mask (that is, the above vessel location labeling information). $L_j$ represents a $J^{th}$ pixel of L. In L, if a location corresponding to the pixel is the vessel, the location is set to 1, or otherwise, the location is set to 0. $\|L\|$ represents a number of pixels in L. $\odot$ represents the element-wise multiplication. $M_{1j}$ and $M_{2j}$ respectively represent $J^{th}$ pixels of the mask-related enhanced image and the mask-related real image.

In a possible implementation, when the sub-loss function value includes at least two of the first sub-loss function value, the second sub-loss function value, and the third sub-loss function value, the acquiring the image enhancement loss function value based on the sub-loss function value includes:

weighting the at least two of the sub-loss function values to obtain the image enhancement loss function value.

Taking the sub-loss function value including the first sub-loss function value, the second sub-loss function value, and the third sub-loss function value as an example, a final optimization function is a weighted combination of the binary cross-entropy loss, the reconstruction loss, the SSIM loss, and the mask loss. The total loss function may be as follows:

$$L=L_{BCE}+\lambda_1 L_{rec}+\lambda_2 L_{ssim}+\lambda_3 L_{mask} \qquad (8).$$

$\lambda_1$, $\lambda_2$, and $\lambda_3$ are respectively used for controlling importance of the losses relative to the binary cross entropy. For example, $\lambda_1$, $\lambda_2$, and $\lambda_3$ may be respectively set to 0.2, 0.4, and 0.2.

$\lambda_1$, $\lambda_2$, and $\lambda_3$ may be pre-set by the developers in the computer device, for example, may be pre-set by the developers in the loss function of the first image processing model.

Step 505: Train the first image processing model based on the loss function value.

In this embodiment of this present disclosure, during the training of the first image processing model based on the loss function value, the computer device may update parameters of the coder based on the vessel classification loss function value and the image enhancement loss function value, update parameters of the first decoder based on the vessel classification loss function value, and update parameters of the second decoder based on the image enhancement loss function value.

That is to say, the computer device may update the parameters of the shared coder through L, update the parameters of the decoder (that is, the first decoder) in the image segmentation branch through $L_{BCE}$, and update the parameters of the decoder (that is, the second decoder) in the image enhancement branch through $\lambda_1 L_{rec}+\lambda_2 L_{ssim}+\lambda_3 L_{mask}$.

In a possible implementation, the updating of the parameters of the coder based on the vessel classification loss function value and the image enhancement loss function value includes:

weighting the vessel classification loss function value and the image enhancement loss function value to obtain a total loss function value; and updating the parameters of the coder based on the total loss function value.

In this embodiment of this present disclosure, in order to more accurately control the impact of the vessel classification and the image enhancement on the coder, the computer device may further weight the vessel classification loss function value and the image enhancement loss function value.

The computer device can set different weights for the vessel classification loss function value and the image enhancement loss function value based on importance of information learned by the image enhancement branch to the vessel classification task during the training of the above coder shared by the image segmentation branch and the image enhancement branch. The weights for the vessel classification loss function value and the image enhancement loss function value may be pre-set by the developers in the computer device, for example, the weights may be pre-set by the developers in the loss function of the first image processing model.

As shown in FIG. 6, during the training of the first image processing model by the loss function values, the computer device may respectively update the parameters of the two branches of the first image processing model through different parts of the loss function value. The vessel classification loss function value (such as $L_{BCE}$ in FIG. 6) in the above loss function value is used for training the image segmentation branch, and the image enhancement loss function value (such as $L_{rec}$, $L_{ssim}$, and $L_{mask}$ in FIG. 6) in the loss function value is used for training the image enhancement branch. Since the image segmentation branch and the image enhancement branch share the coder, the image segmentation branch in the first image processing model can learn the information of the image enhancement part, thereby improving the accuracy of the vessel classification of the low quality image by the image segmentation branch.

Step 506: Generate a second image processing model based on the first image processing model when the first image processing model is trained.

In a possible implementation, the computer device generates the second image processing model based on the image segmentation branch when the first image processing model is trained.

The second image processing model is configured to process an inputted target vessel image to output vessel classification information of the target vessel image, the vessel classification information being used for indicating a target type vessel in the target vessel image, and the target type vessel being at least one of the at least two types of vessels.

In the structure shown in FIG. 6, in an application phase of inference, the image enhancement branch may be abandoned, and only the image segmentation branch is retained for the vessel classification (such as the A/V classification), which can significantly reduce the inference time compared with operating the whole first image processing model.

In a possible implementation, the computer device may input a target vessel image into the second image processing model, and obtain vessel location information outputted by the second image processing model, the vessel location information indicating at least a location of a target type vessel predicted from the target vessel image, and output a vessel classification result image based on the vessel location information, the vessel classification result image being used for indicating the target type vessel in the target vessel image.

In the above embodiment, the model training loss is determined based on not only the image difference and the visual perception difference between the predicted enhanced image and the high quality vessel image sample but also the difference between the masked images respectively corresponding to the predicted enhanced image and the high quality vessel image sample, which helps improve the quality of the model training, thereby improving the accuracy of the subsequent vessel classification using the trained model.

Figure 8:
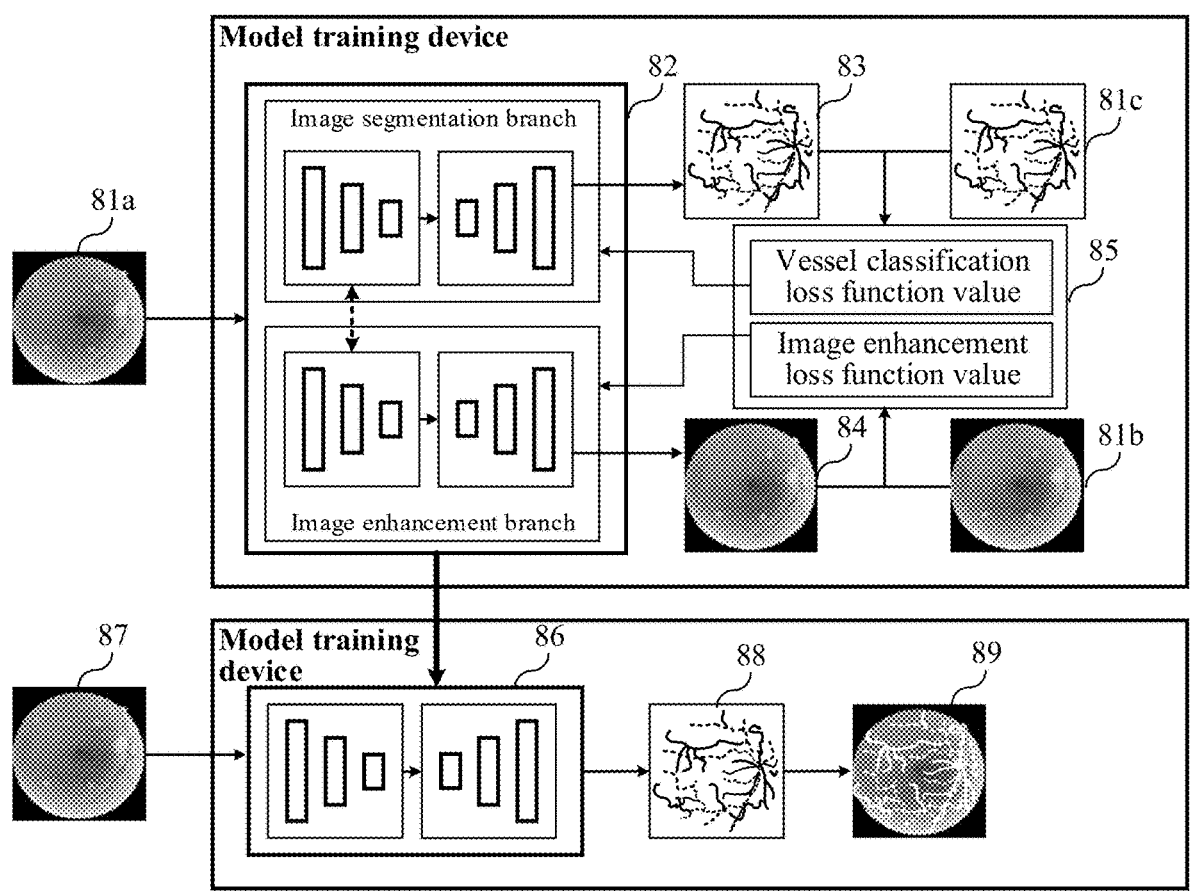
FIG. 8 is a framework diagram of training and application of a fundus image processing model according to an exemplary embodiment.

Taking the above vessel image as the fundus image and the vessel location information as the masked image as an example, FIG. 8 shows a framework diagram of training and application of a fundus image processing model according to an exemplary embodiment. As shown in FIG. 8, the training and the application process of the model for fundus image vessel classification may be as follows:

Firstly, the developers prepare a high quality fundus image sample, processes the high quality fundus image sample 81b through the degradation model, to obtain a low quality fundus image sample 81a, and then performs a labeling operation based on the fundus image sample, to obtain a labeled masked image 81c representing real locations of various types of vessels, and then inputs the high quality fundus image sample 81b, the low quality fundus image sample 81a and the labeled masked image 81c into a model training device as training data.

In a model training phase, the model training device inputs the low quality fundus image sample 81a into a first image processing model 82, outputs a predicted masked image 83 through an image segmentation branch in the first image processing model 82, and outputs a predicted enhanced image 83 through an image enhancement branch in the first image processing model 82. The image segmentation branch and the image enhancement branch share a coder. The model training device calculates a loss function value 85 through the high quality fundus image sample 81b, the labeled masked image 81c, the predicted masked image 83, and the predicted enhanced image 84, updates parameters of the image segmentation branch through a vessel classification loss function value in the loss function value 85, and updates parameters of the image enhancement branch through an image enhancement loss function value in the loss function value 85. Since the image segmentation branch and the image enhancement branch share the coder, during the updating of the parameters, the model training device updates a decoder in the image segmentation branch through the vessel classification loss function value, updates a decoder in the image enhancement branch through the image enhancement loss function value, and updates the shared coder through the vessel classification loss function value and the image enhancement loss function value.

After the model training, the developers may construct a second image processing model 86 through the image segmentation branch in the first image processing model 82, and deploy the second image processing model into a model application device.

In a vessel classification phase, the model application device may receive an inputted target fundus image 87, and input the target fundus image 87 into the second image processing model 86. The second image processing model 86 outputs a corresponding masked image 88, and outputs a fundus image 89 after vessel classification based on the masked image 88.

The fundus image is a non-invasive medical image. Vessels may be observed non-invasively through the fundus image. A morphology change of retinal arteries and veins change may cause various systemic diseases, cardiovascular diseases, and brain diseases. In addition, a biomarker study on retinal vessels shows that progression of diabetic retinopathy is correlated with a relatively large venous diameter. Moreover, it is reported that risks of hypertension and diabetes are correlated with a reduction in a retinal artery diameter. Therefore, the A/V classification lays a foundation for quantitative vessel analysis and facilitates the retinal biomarker study.

In an actual clinical practice, captured fundus images usually have greatly varying quality, which is caused by a plurality of external interference factors, such as a lighting condition, a fundus camera, and uneven levels of technical personnel. For example, artifacts are easily generated during imaging of a fundus image, resulting in a low quality fundus image. Statistics show that 12% of captured fundus images does not have the quality allowing reading by an ophthalmologist during the clinical practice, and low image quality greatly affects the A/V classification performance of the model. For segmentation between arteries and veins in a low quality image, the end-to-end dual-branch network provided in the above embodiment of this present disclosure may include the enhancement branch and the segmentation branch, so that the A/V classification performance can be improved while the image quality is improved. The two branches may share the same coder, so as to reduce the artifacts of the reconstructed image by virtue of the loss of the structural similarity. In this present disclosure, the quality of the reconstructed enhanced image near the vessels may be further emphasized through the mask loss. The vessel classification model constructed through the above dual-branch network can provide more accurate vessel classification, further assist a doctor in the systematic diagnosis of cardiovascular diseases, brain diseases, and the like, and assists the doctor in determining whether a distribution of vessels is normal or not in a fundus screening system, thereby helping prevent and diagnose a fundus disease and a systemic disease such as hypertension and diabetes.

This present disclosure performs an ablation study based on the solutions shown in the above embodiments of this present disclosure to evaluate effectiveness of the plurality of loss functions (that is, the reconstruction loss, the SSIM loss, and the mask loss) in the image enhancement branch when tested with the low quality image. In order to evaluate the A/V classification performance of the solutions provided in this present disclosure, three metrics: accuracy (Acc), sensitivity (Sen), and specificity (Spec) are used in this present disclosure for evaluating the A/V classification performance based on a real vessel pixel-level image, so as to compare effectiveness of different modules under the same criterion.

As shown in Table 1, an accuracy of the A/V classification is improved by 2.15% by adding the image enhancement branch having the reconstruction loss to the image segmentation branch as an auxiliary task, which indicates that the coder can extract more robust features of the low quality image when the image enhancement task is added to the network. In addition to the reconstruction loss, this present disclosure further adds the SSIM loss and the mask loss to the image enhancement branch respectively. After integrating the SSIM loss into the image enhancement branch, the accuracy of the A/V classification is improved by 1.02%. In addition, when the mask loss is used, the accuracy of the A/V classification is improved by 0.90%, which indicates that the mask loss helps the A/V classification task by emphasizing the vessel regions. Finally, the image enhancement branch helps the image segmentation branch realize the best performance for the A/V classification, which realizes an accuracy of 91.52% for the low quality fundus image.

TABLE 1

| Integration mode | | | A/V classification | | |
|---|---|---|---|---|---|
| Reconstruction loss | SSIM loss | Mask loss | Acc | Sen | Spec |
| x | x | x | 88.22 | 85.50 | 90.56 |
| √ | x | x | 90.37 | 88.93 | 91.68 |
| √ | √ | x | 91.39 | 90.50 | 92.28 |
| √ | x | √ | 91.27 | 88.87 | 93.36 |
| √ | √ | √ | 91.52 | 87.94 | 94.53 |

Table 2 shows a comparison between the A/V classification performance of this present disclosure and performance of an A/V classification technology in the related art for a low quality test image in AV-DRIVE and INSPIRE-AVR datasets. In this present disclosure, the method shown in the above embodiments is compared with the current widely used U-Net. In this present disclosure, two U-Net models are trained by using UNet-high quality (UNet-HQ) and UNet-low quality (UNet-LQ) fundus images of the AV-DRIVE dataset respectively. Firstly, performance of the UNet-HQ model is respectively evaluated on the high quality test image and the low quality test image. As shown in the first two rows of Table 2, the performance evaluated by using the low quality test image significantly decreases by 4.66% compared to the performance evaluated by using the high quality test image. Therefore, a huge domain gap exists between the high quality fundus image and the low quality fundus image, which is a main reason for studying the low quality A/V classification in this present disclosure. When the low quality image is used as a training set, the performance of the A/V classification of the UNet-LQ model can be increased by 1.27%. However, a large gap still exists between the performance of the UNet-LQ model and a theoretical upper limit (91.61%, that is, the Acc of the UNet-HQ model tested on the high quality image). In response to the same low quality test image, the accuracy of the A/V classification of the dual-branch network provided in this present disclosure for the AV-DRIVE dataset is 91.52%, which is 3.3% greater than the accuracy of the U-Net model trained on the low quality fundus image. In addition, the performance of the dual-branch network provided in this present disclosure is very close to the theoretical upper limit, with a performance difference of only 0.1%.

For the INSPIRE-AVR dataset, since only A/V labels on centerlines of vessels are provided, but real vessel segmentation is not provided, segmented vessels are evaluated for A/V classification performance. When compared with the U-Net based on the same evaluation criteria and without fine-tuning of the model, the framework presented in this present disclosure outperforms the U-Net, and has an accuracy improvement of 2.53%, which indicates that the method provided in this present disclosure has a generalization ability.

TABLE 2

| Model | Training | Test | AV-DRIVE | | | INSPIRE-AVR | | |
| --- | --- | --- | --- | --- | --- | --- | --- | --- |
| | | | Acc | Sen | Spec | Acc | Sen | Spec |
| U-Net | HQ | HQ | 91.61 | 90.94 | 92.25 | 91.12 | 86.43 | 95.71 |
| | HQ | LQ | 86.95 | 88.53 | 85.75 | 88.58 | 81.27 | 93.95 |
| | LQ | LQ | 88.22 | 85.50 | 90.56 | 90.42 | 89.54 | 91.63 |
| Dual-branch | LQ | LQ | 91.52 | 87.94 | 94.53 | 91.11 | 88.21 | 94.54 |

The solutions shown in the above embodiments of this present disclosure may be implemented or performed in combination with a blockchain. For example, some or all of the steps in the above embodiments may be performed in a blockchain system. Alternatively, the data required for or generated by execution of the various steps in the above embodiments may be stored in the blockchain system. For example, the training sample used in the above model training and the target vessel image and other model input data in the model application process may be acquired from the blockchain system by the computer device. In another example, the parameters of the model obtained after the above model training (including the parameters of the first image processing model and the parameters of the second image processing model) may be stored in the blockchain system.

Figure 9:
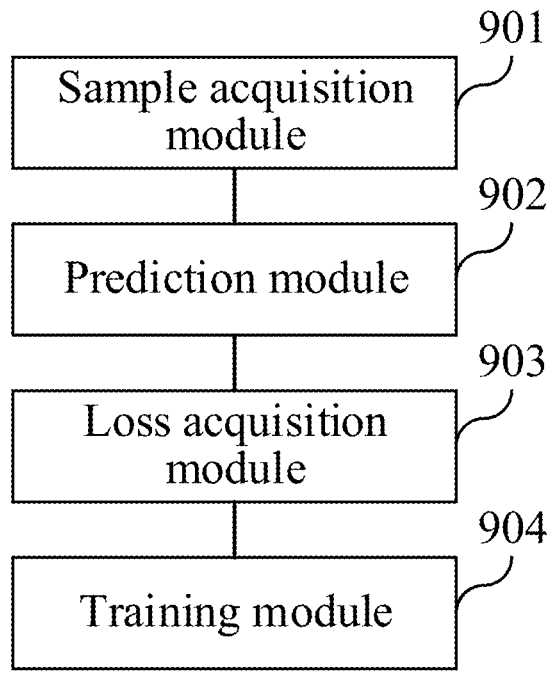
FIG. 9 is a structural block diagram of a vessel image classification apparatus according to an exemplary embodiment.

FIG. 9 is a structural block diagram of a vessel image classification apparatus according to an exemplary embodiment. The apparatus can implement all or part of the steps in the method provided in the embodiment shown in FIG. 2 or FIG. 5. The vessel image classification apparatus includes:

a sample acquisition module 901, configured to acquire a first vessel image sample, a second vessel image sample, and vessel location labeling information, the first vessel image sample being a low quality image corresponding to the second vessel image sample, and the vessel location labeling information being used for indicating locations of at least two types of vessels labeled from the first vessel image sample;

a prediction module 902, configured to input the first vessel image sample into a first image processing model, and obtain a predicted enhanced image and predicted vessel location information outputted by the first image processing model, the predicted enhanced image being a quality-enhanced image of the first vessel image sample; and the predicted vessel location information being used for indicating locations of the at least two types of vessels predicted from the first vessel image sample;

a loss acquisition module 903, configured to acquire a loss function value based on the second vessel image sample, the vessel location labeling information, the predicted enhanced image, and the predicted vessel location information; and a training module 904, configured to train the first image processing model based on the loss function value, the trained first image processing model being configured to generate a second image processing model, the second image processing model being configured to process an inputted target vessel image to output vessel classification information of the target vessel image, the vessel classification information being used for indicating a target type vessel in the target vessel image, and the target type vessel being at least one of the at least two types of vessels.

In a possible implementation, the prediction module 902 includes:

an input sub-module, configured to input the first vessel image sample into the first image processing model;

a segmentation sub-module, configured to process the first vessel image sample through an image segmentation branch in the first image processing model, to obtain the predicted vessel location information outputted by the image segmentation branch; and an enhancement sub-module, configured to process the first vessel image sample through an image enhancement branch in the first image processing model, to obtain the predicted enhanced image outputted by the image enhancement branch.

In a possible implementation, the loss acquisition module 903 includes:

a classification loss acquisition sub-module, configured to acquire a vessel classification loss function value in the loss function value based on the vessel location labeling information and the predicted vessel location information; and an enhancement loss acquisition sub-module, configured to acquire an image enhancement loss function value in the loss function value based on the second vessel image sample and the predicted enhanced image.

In a possible implementation, the enhancement loss acquisition sub-module is configured to:

acquire a sub-loss function value based on the second vessel image sample and the predicted enhanced image, the sub-loss function value including at least one of a first sub-loss function value, a second sub-loss function value, and a third sub-loss function value; and acquire the image enhancement loss function value based on the sub-loss function value, the first sub-loss function value being used for indicating an overall difference between the second vessel image sample and the predicted enhanced image;

the second sub-loss function value being used for indicating a visual perception difference between the second vessel image sample and the predicted enhanced image; and the third sub-loss function value being used for indicating an image difference between vessel sites respectively corresponding to the second vessel image sample and the predicted enhanced image.

In a possible implementation, when the sub-loss function value includes the third sub-loss function value, the enhancement loss acquisition sub-module is configured to:

acquire a first local image based on the second vessel image sample and the vessel location labeling information, the first local image being an image of a vessel site in the second vessel image sample;

acquire a second local image based on the predicted enhanced image and the predicted vessel location information, the second local image being an image of a vessel site in the predicted enhanced image; and acquire the third sub-loss function value based on the first local image and the second local image.

In a possible implementation, the enhancement loss acquisition sub-module is configured to:

weight at least two values of the sub-loss function value when the sub-loss function value includes the at least two of the first sub-loss function value, the second sub-loss function value, and the third sub-loss function value, to obtain the image enhancement loss function value.

In a possible implementation, the image segmentation branch and the image enhancement branch share a coder, the image segmentation branch further includes a first decoder, and the image enhancement branch further includes a second decoder.

The training module 904 includes:

a coder updating sub-module, configured to update parameters of the coder based on the vessel classification loss function value and the image enhancement loss function value;

a first decoder updating sub-module, configured to update parameters of the first decoder based on the vessel classification loss function value; and a second decoder updating sub-module, configured to update parameters of the second decoder based on the image enhancement loss function value.

In a possible implementation, the coder updating sub-module is configured to:

weight the vessel classification loss function value and the image enhancement loss function value to obtain a total loss function value; and update the parameters of the coder based on the total loss function value.

In a possible implementation, the apparatus further includes:

a model generation module, configured to generate the second image processing model based on the image segmentation branch in response to the first image processing model being trained.

In a possible implementation, the apparatus further includes:

an image input module, configured to input the target vessel image into the second image processing model, and obtain vessel location information outputted by the second image processing model, the vessel location information indicating at least a location of the target type vessel predicted from the target vessel image; and a result output module, configured to output a vessel classification result image based on the vessel location information, the vessel classification result image being used for indicating the target type vessel in the target vessel image.

Figure 10:
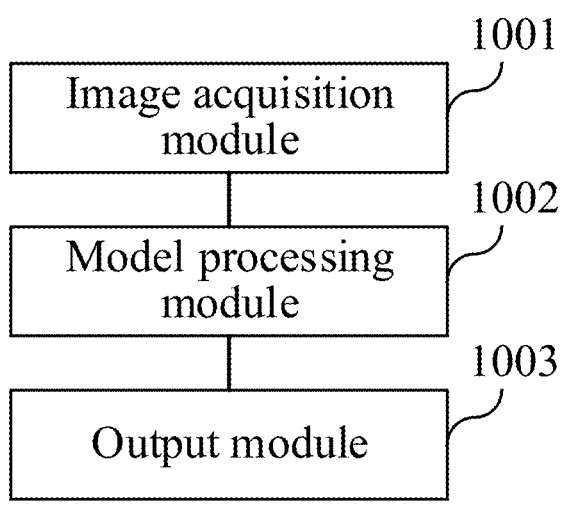
FIG. 10 is a structural block diagram of a vessel image classification apparatus according to an exemplary embodiment.

FIG. 10 is a structural block diagram of a vessel image classification apparatus according to an exemplary embodiment. The vessel image classification apparatus can implement all or part of the steps of the method provided in the embodiment shown in FIG. 3 or FIG. 5. The vessel image classification apparatus includes:

an image acquisition module 1001, configured to acquire a target vessel image;

a model processing module 1002, configured to input the target vessel image into a second image processing model, and obtaining vessel location information outputted by the second image processing model, the vessel location information indicating at least a location of a target type vessel predicted from the target vessel image; and an output module 1003, configured to output a vessel classification result image based on the vessel location information, the vessel classification result image being used for indicating the target type vessel in the target vessel image; and the second image processing model being generated based on a trained first image processing model; a loss function value for training the first image processing model being acquired based on a second vessel image sample, vessel location labeling information, a predicted enhanced image, and predicted vessel location information; the predicted enhanced image and the predicted vessel location information being outputted by the first image processing model after processing the first vessel image sample; the first vessel image sample being a low quality image corresponding to the second vessel image sample, and the vessel location labeling information being used for indicating locations of at least two types of vessels labeled from the first vessel image sample; the predicted enhanced image being a quality-enhanced image of the first vessel image sample; and the predicted vessel location information being used for indicating locations of the at least two types of vessels predicted from the first vessel image sample.

In various embodiments in the present disclosure, a module (or a sub-module) may refer to a software module, a hardware module, or a combination thereof. A software module may include a computer program or part of the computer program that has a predefined function and works together with other related parts to achieve a predefined goal, such as those functions described in this disclosure. A hardware module may be implemented using processing circuitry and/or memory configured to perform the functions described in this disclosure. Each module can be implemented using one or more processors (or processors and memory). Likewise, a processor (or processors and memory) can be used to implement one or more modules. Moreover, each module can be part of an overall module that includes the functionalities of the module. The description here also applies to the term module and other equivalent terms.

Figure 11:
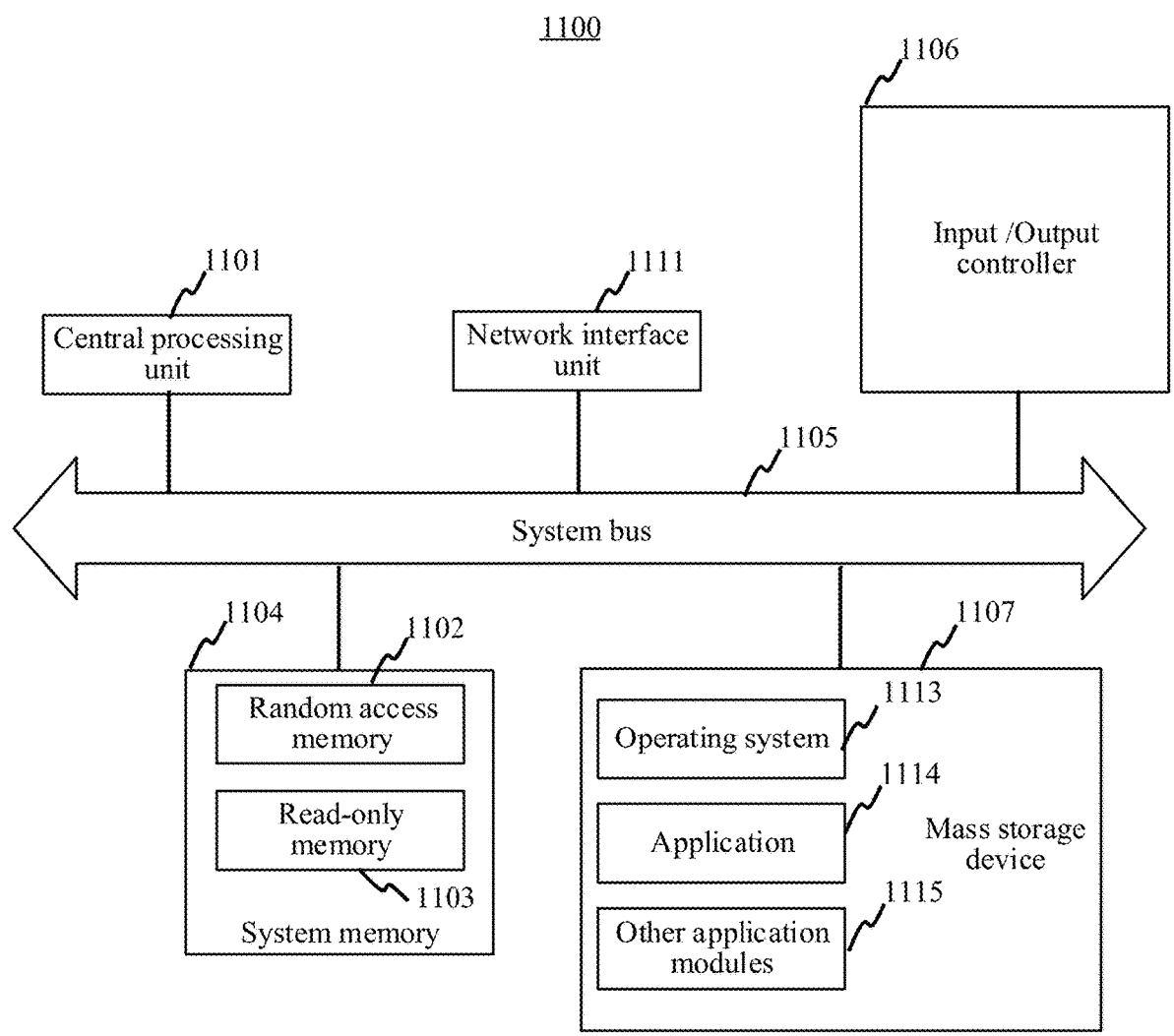
FIG. 11 is a schematic structural diagram of a computer device according to an exemplary embodiment.

FIG. 11 is a schematic structural diagram of a computer device according to an exemplary embodiment. The computer device may be implemented as the computer device configured to train the first image processing model in the method embodiments described above, or may be implemented as the computer device configured to perform the vessel classification through the second image processing model in the method embodiments described above. The computer device 1100 includes a central processing unit (CPU) 1101, a system memory 1104 including a random access memory (RAM) 1102 and a read-only memory (ROM) 1103, and a system bus 1105 connecting the system memory 1104 to the CPU 1101. The computer device 1100 further includes a basic input/output controller 1106 configured to transmit information between components in the computer, and a mass storage device 1107 configured to store an operating system 1113, an application program 1114, and another program module 1115.

The mass storage device 1107 is connected to the CPU 1101 by using a mass storage controller (not shown) connected to the system bus 1105. The mass storage device 1107 and an associated computer-readable medium provide non-volatile storage for the computer device 1100. That is, the mass storage device 1107 may include a computer-readable medium (not shown) such as a hard disk or a compact disc ROM (CD-ROM) drive.

Without loss of generality, the computer-readable medium may include a computer storage medium and a communication medium. The computer storage medium includes volatile and non-volatile media, and removable and non-removable media implemented by using any method or technology and configured to store information such as a computer-readable instruction, a data structure, a program module, or other data. The computer storage medium includes a RAM, a ROM, a flash memory or another solid-state memory technology, a CD-ROM, or another optical memory, a magnetic cassette, a magnetic tape, a magnetic disk memory, or another magnetic storage device. Certainly, those skilled in the art may learn that the computer storage medium is not limited to the above. The foregoing system memory 1104 and mass storage device 1107 may be collectively referred to as a memory.

The computer device 1100 may be connected to the Internet or another network device by using a network interface unit 1111 connected to the system bus 1105.

The memory further includes one or more programs. The one or more programs are stored in the memory. The CPU 1101 executes the one or more programs to implement all or some steps of the method shown in FIG. 2, FIG. 3, or FIG. 5.

In an exemplary embodiment, a non-temporary computer-readable storage medium comprising an instruction, for example, a memory comprising a computer program (an instruction), is further provided, and the program (the instruction) may be executed by a processor in a computer device to complete the method shown in the embodiments of this present disclosure. For example, the non-transitory computer-readable storage medium may be a read-only memory (ROM), a random access memory (random-access memory, RAM), a compact disc read-only memory (CD-ROM), a magnetic tape, a floppy disk, an optical data storage device, and the like.

In an exemplary embodiment, a computer program product or a computer program is further provided. The computer program product or the computer program includes computer instructions, and the computer instructions are stored in a computer-readable storage medium. A processor of a computer device reads the computer instructions from the computer-readable storage medium. The processor executes the computer instructions, so that the computer device performs the method in the foregoing various embodiments.

It is to be understood that this present disclosure is not limited to the precise structures described above and shown in the accompanying drawings, and various modifications and changes can be made without departing from the scope of this present disclosure. The scope of this present disclosure is limited by the appended claims only.

What is claimed is:

1. A method for classifying a vessel image, the method comprising:
    acquiring, by a device comprising a memory storing instructions and a processor in communication with the memory, a first vessel image sample, a second vessel image sample, and vessel location labeling information, the first vessel image sample being a low quality image corresponding to the second vessel image sample, and the vessel location labeling information indicating locations of at least two types of vessels labeled from the first vessel image sample;
    inputting, by the device, the first vessel image sample into a first image processing model, and obtaining a predicted enhanced image and predicted vessel location information outputted by the first image processing model, the predicted enhanced image being a quality-enhanced image of the first vessel image sample, and the predicted vessel location information indicating locations of the at least two types of vessels predicted from the first vessel image sample;
    acquiring, by the device, a loss function value based on the second vessel image sample, the vessel location labeling information, the predicted enhanced image, and the predicted vessel location information; and
    training, by the device, the first image processing model based on the loss function value, the trained first image processing model being configured to generate a second image processing model, the second image processing model being configured to process a target vessel image to output vessel classification information of the target vessel image, the vessel classification information indicating a target type vessel in the target vessel image, and the target type vessel being at least one of the at least two types of vessels.

2. The method according to claim 1, wherein the inputting the first vessel image sample into the first image processing model, and obtaining the predicted enhanced image and the predicted vessel location information outputted by the first image processing model comprises:
    inputting the first vessel image sample into the first image processing model;
    processing the first vessel image sample through an image segmentation branch in the first image processing model, to obtain the predicted vessel location information outputted by the image segmentation branch; and
    processing the first vessel image sample through an image enhancement branch in the first image processing model, to obtain the predicted enhanced image outputted by the image enhancement branch.

3. The method according to claim 2, wherein the acquiring the loss function value based on the second vessel image sample, the vessel location labeling information, the predicted enhanced image, and the predicted vessel location information comprises:
    acquiring a vessel classification loss function value in the loss function value based on the vessel location labeling information and the predicted vessel location information; and
    acquiring an image enhancement loss function value in the loss function value based on the second vessel image sample and the predicted enhanced image.

4. The method according to claim 3, wherein the acquiring the image enhancement loss function value in the loss function value based on the second vessel image sample and the predicted enhanced image comprises:
    acquiring a sub-loss function value based on the second vessel image sample and the predicted enhanced image, the sub-loss function value comprising at least one of a first sub-loss function value, a second sub-loss function value, and a third sub-loss function value; and
    acquiring the image enhancement loss function value based on the sub-loss function value,
    wherein:
        the first sub-loss function value indicates an overall difference between the second vessel image sample and the predicted enhanced image, the second sub-loss function value indicates a visual perception difference between the second vessel image sample and the predicted enhanced image, and
the third sub-loss function value indicates an image difference between vessel sites respectively corresponding to the second vessel image sample and the predicted enhanced image.

5. The method according to claim 4, wherein:
the sub-loss function value comprises the third sub-loss function value; and
the acquiring the sub-loss function value based on the second vessel image sample and the predicted enhanced image comprises:
acquiring a first local image based on the second vessel image sample and the vessel location labeling information, the first local image being an image of a vessel site in the second vessel image sample;
acquiring a second local image based on the predicted enhanced image and the predicted vessel location information, the second local image being an image of a vessel site in the predicted enhanced image; and
acquiring the third sub-loss function value based on the first local image and the second local image.

6. The method according to claim 4, wherein:
the sub-loss function value comprises at least two of the first sub-loss function value, the second sub-loss function value, and the third sub-loss function value; and
the acquiring the image enhancement loss function value based on the sub-loss function value comprises:
weighting the at least two of the sub-loss function values to obtain the image enhancement loss function value.

7. The method according to claim 3, wherein:
the image segmentation branch and the image enhancement branch share a coder, the image segmentation branch further comprises a first decoder, and the image enhancement branch further comprises a second decoder; and
the training the first image processing model based on the loss function value comprises:
updating parameters of the coder based on the vessel classification loss function value and the image enhancement loss function value;
updating parameters of the first decoder based on the vessel classification loss function value; and
updating parameters of the second decoder based on the image enhancement loss function value.

8. A apparatus for classifying a vessel image, the apparatus comprising:
a memory storing instructions; and
a processor in communication with the memory, wherein, when the processor executes the instructions, the processor is configured to cause the apparatus to perform:
acquiring a first vessel image sample, a second vessel image sample, and vessel location labeling information, the first vessel image sample being a low quality image corresponding to the second vessel image sample, and the vessel location labeling information indicating locations of at least two types of vessels labeled from the first vessel image sample,
inputting the first vessel image sample into a first image processing model, and obtaining a predicted enhanced image and predicted vessel location information outputted by the first image processing model, the predicted enhanced image being a quality-enhanced image of the first vessel image sample, and the predicted vessel location information indicating locations of the at least two types of vessels predicted from the first vessel image sample,
acquiring a loss function value based on the second vessel image sample, the vessel location labeling information, the predicted enhanced image, and the predicted vessel location information, and
training the first image processing model based on the loss function value, the trained first image processing model being configured to generate a second image processing model, the second image processing model being configured to process a target vessel image to output vessel classification information of the target vessel image, the vessel classification information indicating a target type vessel in the target vessel image, and the target type vessel being at least one of the at least two types of vessels.

9. The apparatus according to claim 8, wherein, when the processor is configured to cause the apparatus to perform inputting the first vessel image sample into the first image processing model, and obtaining the predicted enhanced image and the predicted vessel location information outputted by the first image processing model, the processor is configured to cause the apparatus to perform:
inputting the first vessel image sample into the first image processing model;
processing the first vessel image sample through an image segmentation branch in the first image processing model, to obtain the predicted vessel location information outputted by the image segmentation branch; and
processing the first vessel image sample through an image enhancement branch in the first image processing model, to obtain the predicted enhanced image outputted by the image enhancement branch.

10. The apparatus according to claim 9, wherein, when the processor is configured to cause the apparatus to perform acquiring the loss function value based on the second vessel image sample, the vessel location labeling information, the predicted enhanced image, and the predicted vessel location information, the processor is configured to cause the apparatus to perform:
acquiring a vessel classification loss function value in the loss function value based on the vessel location labeling information and the predicted vessel location information; and
acquiring an image enhancement loss function value in the loss function value based on the second vessel image sample and the predicted enhanced image.

11. The apparatus according to claim 10, wherein, when the processor is configured to cause the apparatus to perform acquiring the image enhancement loss function value in the loss function value based on the second vessel image sample and the predicted enhanced image, the processor is configured to cause the apparatus to perform:
acquiring a sub-loss function value based on the second vessel image sample and the predicted enhanced image, the sub-loss function value comprising at least one of a first sub-loss function value, a second sub-loss function value, and a third sub-loss function value; and
acquiring the image enhancement loss function value based on the sub-loss function value,
wherein:
the first sub-loss function value indicates an overall difference between the second vessel image sample and the predicted enhanced image,
the second sub-loss function value indicates a visual perception difference between the second vessel image sample and the predicted enhanced image, and the third sub-loss function value indicates an image difference between vessel sites respectively corresponding to the second vessel image sample and the predicted enhanced image.

12. The apparatus according to claim 11, wherein:
the sub-loss function value comprises the third sub-loss function value; and
when the processor is configured to cause the apparatus to perform acquiring the sub-loss function value based on the second vessel image sample and the predicted enhanced image, the processor is configured to cause the apparatus to perform:
acquiring a first local image based on the second vessel image sample and the vessel location labeling information, the first local image being an image of a vessel site in the second vessel image sample;
acquiring a second local image based on the predicted enhanced image and the predicted vessel location information, the second local image being an image of a vessel site in the predicted enhanced image; and
acquiring the third sub-loss function value based on the first local image and the second local image.

13. The apparatus according to claim 11, wherein:
the sub-loss function value comprises at least two of the first sub-loss function value, the second sub-loss function value, and the third sub-loss function value; and
when the processor is configured to cause the apparatus to perform acquiring the image enhancement loss function value based on the sub-loss function value, the processor is configured to cause the apparatus to perform:
weighting the at least two of the sub-loss function values to obtain the image enhancement loss function value.

14. The apparatus according to claim 10, wherein:
the image segmentation branch and the image enhancement branch share a coder, the image segmentation branch further comprises a first decoder, and the image enhancement branch further comprises a second decoder; and
when the processor is configured to cause the apparatus to perform training the first image processing model based on the loss function value, the processor is configured to cause the apparatus to perform:
updating parameters of the coder based on the vessel classification loss function value and the image enhancement loss function value;
updating parameters of the first decoder based on the vessel classification loss function value; and
updating parameters of the second decoder based on the image enhancement loss function value.

15. A non-transitory computer-readable storage medium, storing computer-readable instructions, wherein, the computer-readable instructions, when executed by a processor, are configured to cause the processor to perform:
acquiring a first vessel image sample, a second vessel image sample, and vessel location labeling information, the first vessel image sample being a low quality image corresponding to the second vessel image sample, and the vessel location labeling information indicating locations of at least two types of vessels labeled from the first vessel image sample,
inputting the first vessel image sample into a first image processing model, and obtaining a predicted enhanced image and predicted vessel location information outputted by the first image processing model, the predicted enhanced image being a quality-enhanced image of the first vessel image sample, and the predicted vessel location information indicating locations of the at least two types of vessels predicted from the first vessel image sample,
acquiring a loss function value based on the second vessel image sample, the vessel location labeling information, the predicted enhanced image, and the predicted vessel location information, and
training the first image processing model based on the loss function value, the trained first image processing model being configured to generate a second image processing model, the second image processing model being configured to process a target vessel image to output vessel classification information of the target vessel image, the vessel classification information indicating a target type vessel in the target vessel image, and the target type vessel being at least one of the at least two types of vessels.

16. The non-transitory computer-readable storage medium according to claim 15, wherein, when the computer-readable instructions are configured to cause the processor to perform inputting the first vessel image sample into the first image processing model, and obtaining the predicted enhanced image and the predicted vessel location information outputted by the first image processing model, the computer-readable instructions are configured to cause the processor to perform:
inputting the first vessel image sample into the first image processing model;
processing the first vessel image sample through an image segmentation branch in the first image processing model, to obtain the predicted vessel location information outputted by the image segmentation branch; and
processing the first vessel image sample through an image enhancement branch in the first image processing model, to obtain the predicted enhanced image outputted by the image enhancement branch.

17. The non-transitory computer-readable storage medium according to claim 16, wherein, when the computer-readable instructions are configured to cause the processor to perform acquiring the loss function value based on the second vessel image sample, the vessel location labeling information, the predicted enhanced image, and the predicted vessel location information, the computer-readable instructions are configured to cause the processor to perform:
acquiring a vessel classification loss function value in the loss function value based on the vessel location labeling information and the predicted vessel location information; and
acquiring an image enhancement loss function value in the loss function value based on the second vessel image sample and the predicted enhanced image.

18. The non-transitory computer-readable storage medium according to claim 17, wherein, when the computer-readable instructions are configured to cause the processor to perform acquiring the image enhancement loss function value in the loss function value based on the second vessel image sample and the predicted enhanced image, the computer-readable instructions are configured to cause the processor to perform:
acquiring a sub-loss function value based on the second vessel image sample and the predicted enhanced image, the sub-loss function value comprising at least one of a first sub-loss function value, a second sub-loss function value, and a third sub-loss function value; and acquiring the image enhancement loss function value based on the sub-loss function value, wherein:
- the first sub-loss function value indicates an overall difference between the second vessel image sample and the predicted enhanced image,
- the second sub-loss function value indicates a visual perception difference between the second vessel image sample and the predicted enhanced image, and
- the third sub-loss function value indicates an image difference between vessel sites respectively corresponding to the second vessel image sample and the predicted enhanced image.

19. The non-transitory computer-readable storage medium according to claim 18, wherein:
the sub-loss function value comprises the third sub-loss function value; and
when the computer-readable instructions are configured to cause the processor to perform acquiring the sub-loss function value based on the second vessel image sample and the predicted enhanced image, the computer-readable instructions are configured to cause the processor to perform:
acquiring a first local image based on the second vessel image sample and the vessel location labeling information, the first local image being an image of a vessel site in the second vessel image sample;
acquiring a second local image based on the predicted enhanced image and the predicted vessel location information, the second local image being an image of a vessel site in the predicted enhanced image; and
acquiring the third sub-loss function value based on the first local image and the second local image.

20. The non-transitory computer-readable storage medium according to claim 18, wherein:
the sub-loss function value comprises at least two of the first sub-loss function value, the second sub-loss function value, and the third sub-loss function value; and
when the computer-readable instructions are configured to cause the processor to perform acquiring the image enhancement loss function value based on the sub-loss function value, the computer-readable instructions are configured to cause the processor to perform:
weighting the at least two of the sub-loss function values to obtain the image enhancement loss function value.

* * * * *